United States Patent [19]

Schleich et al.

[11] 4,081,470

[45] Mar. 28, 1978

[54] MANUFACTURE OF POLYENE COMPOUNDS VIA A WITTIG REACTION IN A TWO PHASE SOLVENT SYSTEM

[75] Inventors: Kuno Schleich, Zollikerberg; Hansjörg Stoller, Reinach, both of Switzerland

[73] Assignee: Hoffman-La Roche Inc., Nutley, N.J.

[21] Appl. No.: 711,765

[22] Filed: Aug. 4, 1976

[51] Int. Cl.$^2$ ............................................. C11C 3/02
[52] U.S. Cl. ............................. 260/410.9 R; 260/404; 260/404.5; 260/408; 260/410; 260/345.2; 560/231
[58] Field of Search ............... 260/410.9 V, 410.9 R, 260/410, 404, 488 R, 488 A, 491, 408, 345.2; 560/231

[56] References Cited

U.S. PATENT DOCUMENTS 2,917,523  12/1959  Pommer .................... 260/410.9 V

OTHER PUBLICATIONS

Dehmlow, E. "Phase-Transfer Catalyzed Two-Phase Reactions in Preparative Organic Chemistry" Angew. Chem., Internat. Edit. vol. 13, No. 3 (1974), pp. 170–178.

*Primary Examiner*—Winston A. Douglas
*Assistant Examiner*—John F. Niebling
*Attorney, Agent, or Firm*—Samuel L. Welt; Bernard S. Leon; William H. Epstein

[57] ABSTRACT

Polyene compounds such as vitamin A acetate are prepared by reacting triarylphosphonium salts with aldehydes in a two-phase aqueous-organic solvent system.

9 Claims, No Drawings

MANUFACTURE OF POLYENE COMPOUNDS VIA A WITTIG REACTION IN A TWO PHASE SOLVENT SYSTEM

BACKGROUND OF THE INVENTION

In the manufacture of polyene compounds containing a 3,7-dimethyl-nona-1,3,5,7-tetraen-1-yl group by reacting triarylphosphonium salts with aldehydes (e.g., as used in the manufacture of vitamin A acetate by reacting a β-ionyliden-ethyltriphenylphosphonium halide with γ-acetoxytiglic aldehyde), the reaction has hitherto been carried out in a homogeneous phase using, for example, dimethylformamide, acetonitrile, acetone, dioxane or isopropanol as the solvent. Various disadvantages are encountered when the process is carried out in this manner. In particular, in order to obtain yields which are reasonably satisfactory, the reaction must be carried out at a very low temperature (i.e., at a temperature of below +5° C. to about −30° C.), which requires a substantial cooling capacity. If the reaction is carried out at a temperature greater than +5° C., the yield of end product (e.g., of vitamin A acetate) is considerably reduced (e.g., to about 80%). Furthermore, the proportion of cis-isomers in the end porduct is relatively high.

SUMMARY OF THE INVENTION

It has been found in accordance with this invention that the aforementioned disadvantages of the known process for the manufacture of polyene compounds carrying a 3,7-dimethyl-nona-1,3,5,7-tetraen-1-yl group and also further disadvantages connected with this process can be eliminated by carrying out the reaction in a two-phase, aqueous-organic solvent system, the organic phase consisting of a hydrocarbon or a chlorinated hydrocarbon which is immiscible with water and the volume ratio between the organic phase and water being from about 10:1 to about 1:20.

DETAILED DESCRIPTION OF THE INVENTION

The present invention is based on the foregoing finding and is accordingly concerned with a process for the manufacture of polyene compounds containing a 3,7-dimethyl-nona-1,3,5,7-tetraen-1-yl radical by reacting, via a Wittig reaction, triarylphosphonium salts, preferably triphenylphosphonium salts, with aldehydes, which process comprises carrying out the reaction in a two-phase, aqueous-organic solvent system, the organic phase consisting of hydrocarbon or chlorinated hydrocarbon which is immiscible with water and the volume ratio between the organic phase and water being from about 10:1 to about 1:20.

In the foregoing manner, it is possible to avoid the use of extremely low temperatures during the reaction. The reaction can therefore also be carried out at a temperature of greater than, for example, +5° C., without low yields being obtained. Even at higher temperatures, yields of 93% and more are still achieved.

Furthermore, by using the present process, in particular by applying it to a $C_5 + C_{15}$ vitamin A synthesis and in particular using excess water, the content of the desired trans-isomers is substantially higher while the formation of 9-cis-isomers is simultaneously extensively suppressed. In this manner, if the present process is applied to the manufacture of vitamin A acetate, all-trans-vitamin A acetate is predominantly obtained. The ratio of all-trans to 11-cis is, for example, about 2.3 at 0° C., while this ratio is only 1.2 at −20° C. when the reaction is carried out homogeneously.

Furthermore, in carrying out the present process, the flow of heat from the reaction mixture is less problematic, since one of the components of the solvent system is water. Because of the unproblematic flow of heat, it is also possible to carry out the reaction using high concentrations of the reactants.

It is also of advantage that the reaction mixture obtained according to the present process can be isomerized by customary methods, the all-trans-isomer being obtained in crystalline form in a simple manner.

A further advantage of the present process consists in that relatively cheap bases (e.g., sodium hydroxide solution) can be used as the bases required in the reaction.

In accordance with this invention, the volume ratio of the organic phase to water is in the ratio of from about 10:1 to 1:20.

In general, the volume ratio between the organic phase and water is preferable about 1:1 to 1:10 with from about 5:1 to about 1:5 being especially preferred. According to a particularly preferred embodiment of the present process, an aqueous-organic solvent system is used in which water is present in excess; for example, a solvent system in which the volume ratio between the organic phase and water is about 1:4.

The organic phase of the aqueous-organic solvent system is conveniently an aromatic hydrocarbon (e.g., benzene or toluene) or, preferably, a chlorinated hydrocarbon, especially methylene chloride, ethylene chloride or chlorobenzene. Methylene chloride is particularly preferred. It is essential that the organic solvent is immiscible with water.

The reaction is carried out utilizing the conditions conventional in Wittig reactions. In this regard, temperatures of from about −10° C to about 100° C are generally utilized. It is generally preferred to use a temperature of from about 0° C to 60° C with temperatures of from about 0° C to 30° C being especially preferred.

Depending on the temperature used and the purity of the triarylphosphonium salt used, the reaction time can vary within wide limits; for example, from about 2 minutes to about 120 minutes. If desired, the reaction can be carried out for excessive periods of time, i.e. 120 minutes or greater without deleteriously affecting the reaction.

It is known that the presence of bases in a Wittig reaction is required for the reaction of triarylphosphonium salt with an aldehyde. In the present process, inorganic bases, such as alkali metal hydroxides and alkaline earth metal hydroxides, preferably sodium hydroxide and potassium hydroxide, or substances having a basic reaction, such as alkali metal carbonates (e.g., potassium carbonate) or ammonia or organic amines, preferably tertiary organic amines (e.g., trialkylamines such as triethylamine), are conveniently used. It has proved particularly convenient to add the base (e.g., aqueous sodium hydroxide solution) slowly dropwise to the reaction mixture so that always only a small concentration thereof prevails, and the pH value should be in the range between about 8 and 12.

The customary triarylphosphonium salts (e.g., halides, such as the chloride or the hydrogen sulfate) can be used as β-ionylidenethyltriphenylphosphonium salts.

The reaction is conveniently carried out under the atmosphere of an inert gas (e.g., argon) and with protection against light.

Furthermore, it has proved to be expedient to add to the reaction mixture an antioxidant (e.g., butylated hydroxytoluene or butylated hydroxyanisole).

The present process can be carried out both batchwise and continuously.

Examples of polyene compounds, containing a 3,7-dimethyl-nona-1,3,5,7-tetraen-1-yl group, which can be manufactured by the prsent process are compounds of the general formula

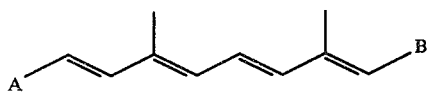

I wherein A is 2,6,6-trimethylcyclohex-1-enyl or substituted phenyl and B is a group of the general formula

 Ia

 Ib or

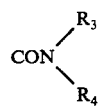 Ic wherein $R_1$ is alkanoyl, $R_2$ is alkyl and $R_3$ and $R_4$ are hydrogen or lower alkyl.

The alkanoyl group, $R_1$, preferably contains up to 18 carbon atoms such as acetyl, propionyl, butyryl, valeroyl, caproyl or palmitoyl. Acetyl is preferred.

The alkyl group, $R_2$, preferably contains up to 10 carbon atoms such as methyl, ethyl, propyl, isopropyl, butyl, pentyl or decyl. In an especially preferred aspect, $R_2$ is methyl or ethyl.

Lower alkyl groups $R_3$ and $R_4$ contain up to 7 carbon atoms such as methyl, ethyl, propyl, isopropyl or heptyl. Methyl and ethyl are preferred.

If A in formula I represents 2,6,6-trimethylcyclohex-1-enyl, the compounds of formula I are derivatives of vitamin A alcohol and vitamin A acid. The manufacture of these compounds, in particular the manufacture of vitamin A acetate, is particularly preferred.

Examples of substituted phenyl groups represented by A are groups of the general formula

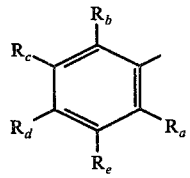

Id wherein $R_a$ and $R_b$ are lower alkyl; $R_c$ is hydrogen or halogen or lower alkyl, lower alkoxy, lower alkenoxy, nitro, amino, mono(lower alkyl)amino, di(lower alkyl)amino, lower alkanoylamido or a N-heterocyclic group; $R_d$ is hydrogen or lower alkyl, lower alkenyl, lower alkoxy, lower alkenoxy, nitro, amino, mono(lower alkyl)amino, di(lower alkyl)amino, lower alkanoylamido or a N-heterocyclic group; and $R_e$ is hydrogen or halogen or lower alkyl, lower alkenyl, lower alkoxy, lower alkenoxy, nitro, amino, mono(lower alkyl)amino, di(lower alkyl)amino, lower alkanoylamido or a N-heterocyclic group with the proviso that at least one of $R_c$, $R_d$ and $R_e$ is other than hydrogen; and with the further proviso that when $R_c$ or $R_e$ is halogen, $R_d$ is other than lower alkoxy.

Compounds of formula I in which A is a substituted phenyl group of formula Id include 9-(4-methoxy-2,3,6-trimethylphenyl)-3,7-dimethyl-nona-2,4,6,8-tetraene-1-acid ethyl ester and 9-(4-methoxy-2,3,6-trimethylphenyl)-3,7-dimethylnona-2,4,6,8-tetraene-1-acid ethylamide. These compounds are described, for example, in U.S. Patent Application Ser. No. 601,148 filed Aug. 1, 1975, now abandoned.

Further examples of substituted phenyl groups represented by A are groups of the general formula

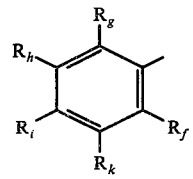

Ie wherein one of the symbol pairs $R_f$ and $R_k$, $R_g$ and $R_h$, $R_h$ and $R_i$ or $R_i$ and $R_K$ are linked together to form a trimethylene, tetramethylene, 1,3-butadienylene, oxytrimethylene or 3-oxypropenylene ring, said rings being optionally substituted by one or more lower alkyl groups, and the remaining symbols each represent hydrogen, halogen, lower alkyl, lower alkenyl, lower alkoxy, lower alkenoxy, nitro, amino, mono(lower alkyl) amino, di(lower alkyl)amino or a N-heterocyclic group with the proviso that at least one of said symbols is other than hydrogen.

Examples of compounds are 9-(4,6-dimethyl-indan-5-yl)-3,7-dimethyl-nona-2,4,6,8-tetraene-1-acid ethyl ester, 9-(4-methoxy-2,3-dimethyl-naphthalene- 5-yl)-3,7-dimethyl-nona-2,4,6,8-tetraene-1-acid ethyl ester and 9-(5,7,8-trimethyl-chromen-6-yl)-3,7-dimethyl-nona-2,4,6,8-tetraene-1-acid methyl ester, which are described in Belgian Pat. Specification No. 818,648.

A third group of examples of substituted phenyl groups reprsented by A are groups of the general formula

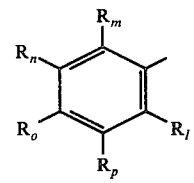

If wherein one of $R_l$ and $R_m$ is halogen or lower alkyl and the other is halogen or lower alkoxy, $R_n$ and $R_p$ are hydrogen, halogen or lower alkyl, $R_o$ is halogen, lower alkoxy, amino, mono(lower alkyl)amino or di(lower alkyl)amino; with the proviso that one of $R_n$ and $R_p$ is other than a halogen.

Examples of compounds wherein A is of the formula If are 9-(2-chloro-4-methoxy-3,5,6-trimethyl-phenyl)-3,7-dimethyl-nona-2,4,6,8-tetraene-1-acid ethyl ester and 9-(2,6-dichloro-4-methoxyphenyl)-3,7-dimethyl-nona-2,4,6,8-tetraene-1-acid ethyl ester.

The synthesis of the polyene compounds which can be prepared by the present invention can be carried out in a variety of ways depending on the number of carbon atoms which are contained in the triarylphosphonium salt and aldehyde reaction components. In the preparation of vitamin A derivatives, that is to say of compounds of formula I in which A is 2,6,6-trimethyl-cyclohex-1-enyl, the reaction can be carried out, for example, according to the procedure $C_{15} + C_5$; $C_{10} + C_{10}$ or $C_{13} + C_7$, it being particularly advantageous to use the $C_{15} + C_5$ procedure; for example, the reaction of a $C_{15}$-triarylphosphonium salt with a $C_5$-aldehyde.

Thus, the process of the present invention can be carried out by reacting a phosphonium salt of the formula

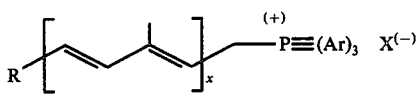

with an aldehyde of the formula

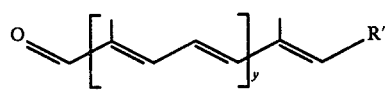

wherein the above formulae Ar is aryl; one of R and R' is A and the other is B; A and B have the above meaning; $X^{(-)}$ is an anion, e.g., a halide or hydrogen sulfate; and x and y and 0 or 1 with the proviso that $x + y$ is 1.

In a preferred aspect, x is 1 and y is 0. In another embodiment of the invention, the process is carried out by applying the $C_{13} + C_7$ principle, i.e., by reacting a phosphonium salt of the formula

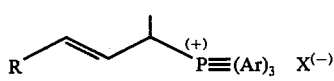

with an aldehyde of the formula

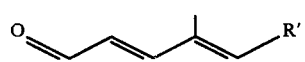

wherein R, R' and $X^{(-)}$ have the above meaning.

In the manufacture of vitamin A acetate under the conditions of the present process, it has proved to be particularly advantageous to react a β-ionylidenethyl-triarylphosphonium salt, preferably a β-ionylidenethyl-triphenylphosphonium salt (e.g., the chloride or hydrogen sulfate), with γ-acetoxytiglic aldehyde.

The following examples illustrate the present invention.

EXAMPLE 1

15 g. of β-ionylidenethyltriphenylphosphonium chloride, 4.5 g. of γ-acetoxytiglic aldehyde and 80 mg. of butylated hydroxytoluene are suspended in 5 ml. of methylene chloride at room temperature. 40 ml. of water are then added to the suspension, after which 1.9 g. of potassium hydroxide dissolved in 10 ml. of water are added over a period of 16 minutes, while stirring vigorously. After completion of the addition of the potassium hydroxide solution, the mixture is stirred for a further 15 minutes. The methylene chloride phase is then separated off and washed with 100 ml. of water until neutral. The methylene chloride is the evaporated off and the mixture is distributed between methanol/water and hexane. After evaporation of the hexane, 9.84 g. (100%) of a mixture of vitamin A acetate isomers having the following composition are obtained:

| | |
|---|---|
| 11,13-di-cis-vitamin A acetate | 0.4 % |
| 11-cis-vitamin A acetate | 35.7 % |
| 13-cis-vitamin A acetate | 0.3 % |
| 9-cis-vitamin A acetate | 0.5 % |
| all-trans-vitamin A acetate | 61.2 % |

The following table summarizes the results of experiments which were carried out under various reaction conditions (temperature and ratio between water and organic phase).

Table

| Parts of $H_2O$ | Parts of $CH_2Cl_2$ | Temp. (° C.) | 9-cis % | 11-cis % | all-trans % |
|---|---|---|---|---|---|
| 1 | 1 | 0 | 2 | 38 | 59 |
| 8 | 1 | 0 | <0.4 | 28 | 72 |
| 5 | 1 | 0 | <0.4 | 31 | 69 |
| 8 | 1 | 20 | <0.4 | 36 | 61 |

In all of these experiments the total yield was between 95% and 100%.

EXAMPLE 2

15. g. of β-ionylidenethyltriphenylphosphonium chloride and 4.5 g. of γ-acetoxytiglic aldehyde are added to a mixture of 40 ml. of water and 10 ml. of methylene chloride in a 100 ml. 4-necked flask which is in an icebath and is provided with a stirrer, thermometer and dropping funnel at 0° C. and under an atmosphere of argon. 1.87 g. of potassium hydroxide dissolved in 10 ml. of water are added dropwise to the mixture obtained over a period of 15 minutes while stirring. After completion of the addition of the potassium hydroxide solution, the mixture is stirred for a further 15 minutes. It is then neutralized with 1 ml. of 2-N acetic acid, placed in a separating funnel and 100 ml. of methanol are added and the mixture is subsequently extracted by shaking three times with 100 ml. of hexane each time. The combined hexane phases are washed with 50 ml. of methanol/water (80:20 by volume). The hexane phases are then dried and evaporated under reduced pressure for about 1 hours. 9.54 g. (97%) of vitamin A acetate having the following isomer composition are obtained:

| | |
|---|---|
| 11-cis-vitamin A acetate | 36.5% |
| 9-cis vitamin A acetate | 0.7% |
| all-trans-vitamin A acetate | 62.9% |

EXAMPLE 3

The process was carried out in an analogous manner to that described in Example 2, but 80 ml. of water and 5 ml. of methylene chloride were used as the solvent system. 9.68 g. (98.4%) of a vitamin A acetate isomer mixture having the following composition were obtained: 9-cis: 0.4%, 11-cis: 32.5% and all-trans: 66.3%.

EXAMPLE 4

The process was carried out in an analogous manner to that described in Example 2, but, in place of 15 g. of β-ionylidenethyltriphenylphosphonium chloride, 16.9 g. of β-ionylidenethyltriphenylphosphonium hydrogen sulfate were used and in place of 1.87 g. of potassium hydroxide, 7.5 g. of potassium carbonate were used. After adding the aqueous (10 ml. of water) potassium carbonate solution over a period of 10 minutes, the mixture was stirred for a further 1 hour. 9.69 g. (98.5%) of a vitamin A acetate isomer mixture having the following composition were obtained: 9-cis: 0.4%; 11-cis: 35.5%; and all-trans: 62.5%.

EXAMPLE 5

19 g. of β-ionylidenetriphenylphosphonium chloride and 7 g. of 6-acetoxy-4-methyl-hexa-2,4-dien-1-al are added to 40 ml. of water and 10 ml. of methylene chloride at 0° C. 2.69 g. of potassium hydroxide dissolved in 7 ml. of water are added to the resulting mixture over a period of 10 minutes while stirring and the mixture is then stirred for a further 1 hour at 0° C. After working up the mixture according to the foregoing examples, 12.7 g. (97%) of vitamin A acetate having the following isomer composition are obtained: 9-cis; 53%; all-trans: 45%.

EXAMPLE 6

10.54 g. of 5-(4-methoxy-2,3,6-trimethylphenyl)-3-methyl-penta-2,4-diene-1-triphenylphosphonium chloride and 2.84 g. of oxosenecioic acid ethyl ester are added to 5 ml. of methylene chloride and 20 ml. of water at 0° C. 1.34 g. of potassium hydroxide dissolved in 3 ml. of water are added dropwise over a period of 15 minutes while stirring and the mixture is stirred for a further 1 hour at 0° C. After working up the mixture according to the foregoing examples, 6.9 g. (98%) of 9-(4-methoxy-2,3,6-trimethyl-phenyl)-3,7-dimethyl-nona-2,4,6,8-tetraene-1-acid ethyl ester containing 52% of the 11-cis-isomer and 47.4% of the all-trans-isomer are obtained.

We claim:

1. In a process for the preparation of polyene compounds containing a 3,7-dimethyl-nona-1,3,5,7-tetraen-1-yl group by reacting, via a Wittig synthesis, triarylphosphonium salts with aldehydes, the improvement which comprises carrying out the Wittig reaction in a two-phase, aqueous-organic solvent system, the organic phase consisting of a hydrocarbon or a chlorinated hydrocarbon which is immiscible with water and the volume ratio between the organic phase and water being from about 10:1 to about 1:20.

2. A process as in claim 1 wherein a triarlyphosphonium salt of the formula

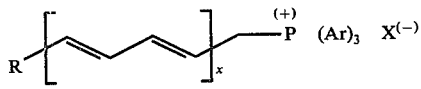

is reacted with an aldehyde of the formula

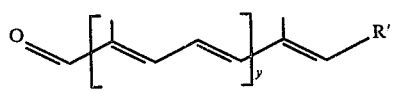

wherein x and y are o or 1 with the proviso that the sum of x + y is 1; Ar is aryl; one of R and R' is A and the other is B; X$^{(-)}$ is an anion; B is a group of the general formula:

—CH$_2$OR$_1$;

—COOR$_2$; or

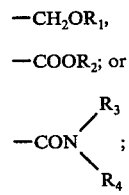

R$_1$ is alkanoyl; R$_2$ is alkyl; R$_3$ and R$_4$ are hydrogen or alkyl; A is 2,6,6-trimethylcyclohex-1-enyl or a substituted phenyl of the formula

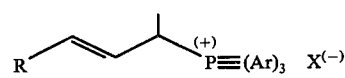

wherein R$_a$ and R$_b$ are lower alkyl; R$_c$ is hydrogen or halogen or lower alkyl, lower alkoxy, lower alkenoxy, nitro, amino, mono(lower alkyl)amino, di(lower alkyl)amino, lower alkanoylamide or a N-heterocyclic group; R$_d$ is hydrogen or lower alkyl, lower alkenyl, lower alkoxy, lower alkenoxy, nitro, amino, mono(lower alkyl)amino, di(lower alkyl)amino, lower alkanoylamido or a N-heterocyclic group; and R$_e$ is hydrogen or halogen or lower alkyl, lower alkenyl, lower alkoxy, lower alkenoxy, nitro, amino, nono(lower alkyl)amino, di(lower alkyl)amino, lower alkanoylamide or a N-heterocyclic group with the proviso that at least one of R$_c$, R$_d$ and R$_e$ is other than hydrogen; and with the further proviso that when R$_c$ or R$_e$ is halogen, R$_d$ is other than lower alkoxy.

3. A process as in claim 1 wherein a triarylphosphonium salt of the formula

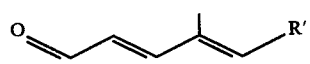

is reacted with an aldehyde of the formula

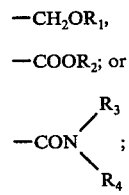

wherein X$^{(-)}$ is an anion; Ar is aryl; one of R and R' is A and the other B; B is a group of the formula

—CH$_2$OR$_1$,

—COOR$_2$; or

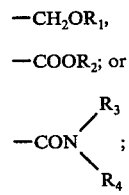

wherein R$_1$ is alkanoyl; R$_2$ is alkyl and R$_3$ and R$_4$ are hydrogen or lower alkyl; A is 2,6,6-trimethylcyclohex-1-enyl or a substituted phenyl of the formula:

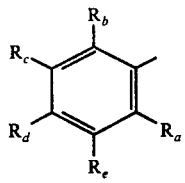

wherein $R_a$ and $R_b$ are lower alkyl; $R_c$ is hydrogen or halogen or lower alkyl, lower alkoxy, lower alkenoxy, nitro, amino, mono(lower alkyl)amino, di(lower alkyl)amino, lower alkanoylamido or N-heterocyclic; $R_d$ is hydrogen, lower alkyl, lower alkenyl, lower alkoxy, lower alkenoxy, nitro, amino, mono(lower alkyl)amino, di)lower alkyl)amino, lower alkanoylamido or N-heterocyclic; and $R_e$ is hydrogen, halogen, lower alkyl, lower alkenyl, lower alkoxy, lower alkenoxy, nitro, amino, mono(lower alkyl)amino, di(lower alkyl)amino, lower alkanoylamido or N-hetercyclic with the proviso that at least one of $R_c$, $R_d$ and $R_e$ is other than hydrogen; and with the further proviso that when $R_c$ or $R_e$ is halogen, $R_d$ is other than lower alkoxy.

4. A process as in claim 1, wherein the triarylphosphonium salts are triphenylphosphonium salts.

5. A process as in claim 1 wherein the volume ratio between the organic phase and water is about 1:1 to 1:10.

6. A process as in claim 1 wherein the organic phase of the aqueous-organic solvent system is a chlorinated hydrocarbon.

7. The process of claim 1 for the manufacture of vitamin A acetate wherein a β-ionylidenethyltriarylphosphonium salt is reacted with γ-acetoxytiglic aldehyde.

8. The process of claim 1 for the preparation of 9-(4-methoxy-2,3,6-trimethyl-phenyl)-3,7-dimethyl-nona-2,4,6,8-tetraene-1-acid ethyl ester wherein 5-(4-methoxy-2,3,6-trimethylphenyl-3-methyl-penta-2,4-diene-1-triphenylphosphonium chloride is reacted with oxosenecioic acid ethyl ester.

9. The process of claim 1 for the preparation of vitamin A acetate wherein β-ionylidenetriphenylphosphonium chloride is reacted with 6-acetoxy-4-methyl-hexa-2,4-dien-1-al.

* * * * *

UNITED STATES PATENT AND TRADEMARK OFFICE
CERTIFICATE OF CORRECTION

PATENT NO. : 4,081,470
DATED : March 28, 1978
INVENTOR(S) : Kuno Schleich and Hansjörg Stoller It is certified that error appears in the above-identified patent and that said Letters Patent are hereby corrected as shown below:

Coversheet, after "[22] Filed: Aug. 4, 1976" insert

[30] Foreign Application Priority Data

Aug. 22, 1975   Switzerland   10907/75

Column 7, claim 2 in the formula, lines 51-57,

"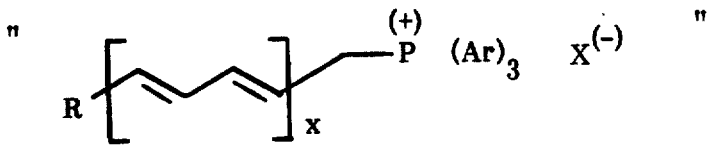"

should be

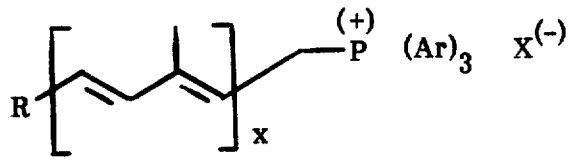

UNITED STATES PATENT AND TRADEMARK OFFICE
CERTIFICATE OF CORRECTION

PATENT NO. : 4,081,470

DATED : March 28, 1978

INVENTOR(S) : Kuno Schleich and Hansjörg Stoller

It is certified that error appears in the above–identified patent and that said Letters Patent are hereby corrected as shown below:

Column 8, claim 2, line 34,

"nono(lower alkyl- "

should be mono(lower alkyl-

Column 9, claim 3, line 16,

"di)lower alkyl)amino, "

should be di(lower alkyl)amino,

Column 9, claim 3, line 20,

"N-hetercyclic"

should be

N-heterocyclic

Signed and Sealed this

Fourth Day of December 1979

[SEAL]

Attest:

SIDNEY A. DIAMOND

Attesting Officer

Commissioner of Patents and Trademarks